(12) United States Patent
Bocca

(10) Patent No.: US 10,433,948 B2
(45) Date of Patent: Oct. 8, 2019

(54) BREAST IMPLANT

(71) Applicant: George Bocca, Austin, TX (US)

(72) Inventor: George Bocca, Austin, TX (US)

(*) Notice: Subject to any disclaimer, the term of this patent is extended or adjusted under 35 U.S.C. 154(b) by 143 days.

(21) Appl. No.: 15/651,662

(22) Filed: Jul. 17, 2017

(65) Prior Publication Data

US 2019/0015194 A1    Jan. 17, 2019

(51) Int. Cl.
| | | |
|---|---|---|
| *A61F 2/12* | (2006.01) | |
| *A61B 17/00* | (2006.01) | |
| *A61L 27/18* | (2006.01) | |
| *A61L 27/02* | (2006.01) | |
| *A61L 27/06* | (2006.01) | |
| *A61L 27/04* | (2006.01) | |
| *A61B 17/064* | (2006.01) | |

(52) U.S. Cl.
CPC .............. *A61F 2/12* (2013.01); *A61B 17/00* (2013.01); *A61L 27/025* (2013.01); *A61L 27/042* (2013.01); *A61L 27/06* (2013.01); *A61L 27/18* (2013.01); *A61B 2017/00796* (2013.01); *A61B 2017/0648* (2013.01); *A61F 2210/0057* (2013.01); *A61F 2220/0016* (2013.01); *A61F 2220/0075* (2013.01); *A61F 2250/0003* (2013.01); *A61F 2250/0013* (2013.01); *A61L 2430/04* (2013.01)

(58) Field of Classification Search
CPC ......................................................... A61F 2/12
USPC ............................................................. 623/7–8
See application file for complete search history.

(56) References Cited

U.S. PATENT DOCUMENTS

| | | | | |
|---|---|---|---|---|
| 2010/0204791 | A1* | 8/2010 | Shfaram | A61B 17/0401 623/8 |
| 2016/0082235 | A1* | 3/2016 | Mosharrafa | A61M 29/02 606/192 |
| 2018/0303599 | A1* | 10/2018 | Al-Jasim | B29C 41/14 |
| 2019/0000608 | A1* | 1/2019 | Renke | B29C 41/22 |

* cited by examiner

*Primary Examiner* — Suzette J Gherbi
(74) *Attorney, Agent, or Firm* — Meyertons, Hood, Kivlin, Kowert & Goetzel, P.C.; Mark R. DeLuca

(57) ABSTRACT

A more versatile and anatomically correct breast implant is described. The breast implant comprises a container filled with a liquid or gel filling material and a support member coupled to the container, wherein the support member is an integral part of the container.

20 Claims, 3 Drawing Sheets

BREAST IMPLANT

BACKGROUND OF THE INVENTION

1. Field of the Invention

The invention generally relates to breast implants.

2. Description of the Relevant Art

Breast implants are well known and are commonly used for reconstructive purposes or for cosmetic reasons to augment the size of a breast. Generally, breast prostheses are made up of an elastomeric material that defines a closed space containing a liquid or semi-liquid material. The most common materials that are used in breast implants are saline solutions or silicone gels.

Breast implants are generally positioned within the chest in one of two positions: (1) implant over the pectoralis major muscle and under the subglandular breast tissue; (2) implant under the pectoralis muscle. Presently there are very few techniques to reliably maintain the position of implants placed as part of cosmetic or reconstructive surgical procedures. Implant malposition may be the result of several factors, including poor surgical technique, i.e. the implant pocket is too big or too low; implant weight; or lack of soft tissue support.

Displacement of the breast implant from the proper position can lead to an unnatural appearance of the breasts. Typical cosmetic effects that can occur for breast implants that have been displaced from the original position include symmastia (movement of the implant toward the center of the chest), lateral displacement (movement of the implant into the armpit region) and inferior displacement (movement of the implant below the breast tissue.

To overcome some of these issues, surgeons may anchor the implant to the soft tissue of the patient. Typically a single anchoring point is used to maintain the position of the breast implant. While this can be effective in preventing displacement of the breast implant, the use of a single anchoring point can lead to unnatural movement of the breast implant, since a natural breast has more than one natural anchoring point within the chest cavity. It is therefore desirable to provide a breast implant that has more than one point of attachment, thereby achieving a more natural looking shape and movement.

SUMMARY OF THE INVENTION

In an embodiment, a breast implant for altering the appearance of a patient's breast includes: a container composed of an elastomeric material, the container defining an inner cavity, wherein the inner cavity is filled with a liquid or gel filling material; and a support member coupled to the container, wherein the support member is an integral part of the container. In some embodiments, the inner cavity may be filled with a saline solution or a silicone gel.

In an embodiment, the support member contacts the container over a majority of a longitudinal axis of the container. The support member may be couplable to two or more ribs of the patient. The support member may include one or more biocompatible hooks that couple the support to the ribs of the patient. Alternatively, or in addition, the support member may include one or more fasteners that can be connected to the ribs of the patient. The support member is composed of a biocompatible polymer.

In some embodiments, the container comprises a stichable region, wherein the stichable region receives threading that is used to alter the shape of the container and/or provide additional support for the container. In some embodiments, the container comprises a port, wherein liquid or gel filling material may be inserted or removed from the container through the port.

In an embodiment, a method of altering the appearance of a patient's breast includes: coupling a support member of a breast implant, as described above, to two or more of the ribs of the patient. In an embodiment, the breast implant is implanted over the pectoralis major muscle and under the subglandular breast tissue. In another embodiment, the breast implant is implanted under the pectoralis muscle. In some embodiments, coupling the support member to two or more ribs comprises attaching two or more hooks of the support member to the ribs of the patient.

BRIEF DESCRIPTION OF THE DRAWINGS

Advantages of the present invention will become apparent to those skilled in the art with the benefit of the following detailed description of embodiments and upon reference to the accompanying drawings in which.

Figure 1:
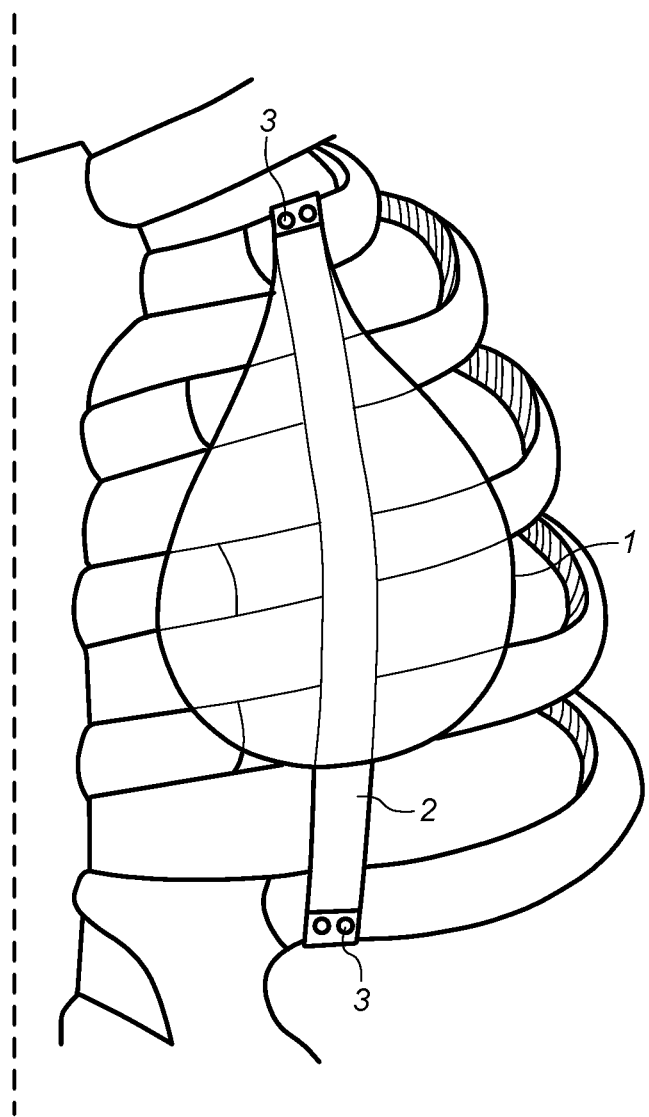
FIG. 1 depicts a side view of a breast implant coupled to a support member.

While the invention may be susceptible to various modifications and alternative forms, specific embodiments thereof are shown by way of example in the drawings and will herein be described in detail. The drawings may not be to scale. It should be understood, however, that the drawings and detailed description thereto are not intended to limit the invention to the particular form disclosed, but to the contrary, the intention is to cover all modifications, equivalents, and alternatives falling within the spirit and scope of the present invention as defined by the appended claims.

DETAILED DESCRIPTION OF THE PREFERRED EMBODIMENTS

It is to be understood the present invention is not limited to particular devices or methods, which may, of course, vary. It is also to be understood that the terminology used herein is for the purpose of describing particular embodiments only, and is not intended to be limiting. As used in this specification and the appended claims, the singular forms "a", "an", and "the" include singular and plural referents unless the content clearly dictates otherwise. Furthermore, the word "may" is used throughout this application in a permissive sense (i.e., having the potential to, being able to), not in a mandatory sense (i.e., must). The term "include," and derivations thereof, mean "including, but not limited to." The term "coupled" means directly or indirectly connected.

Figure 2:
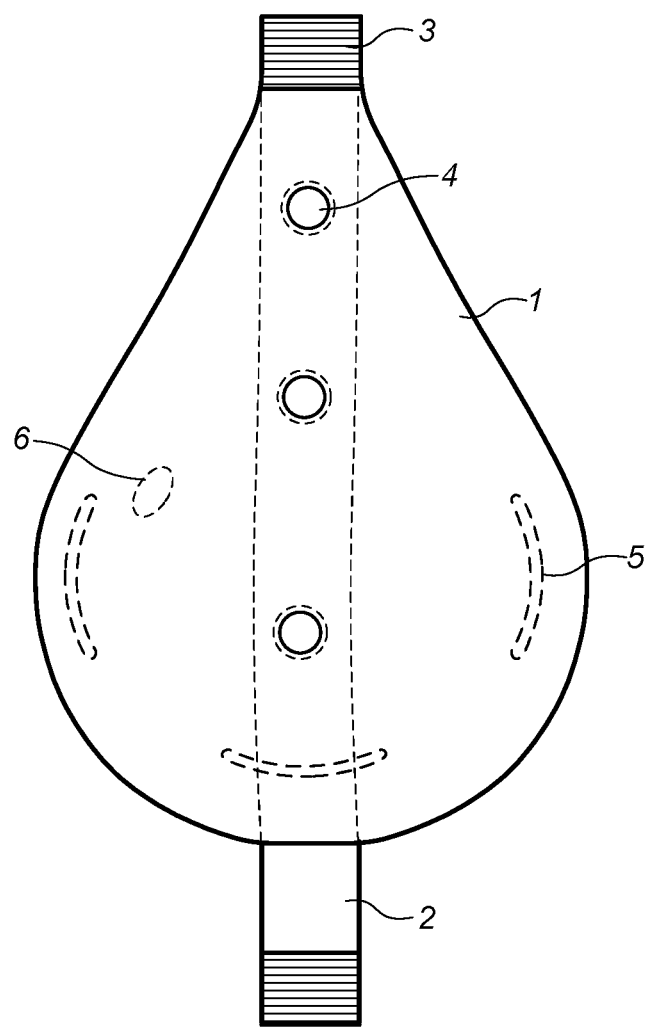
FIG. 2 depicts a front view of a breast implant coupled to a support member.
Figure 3:
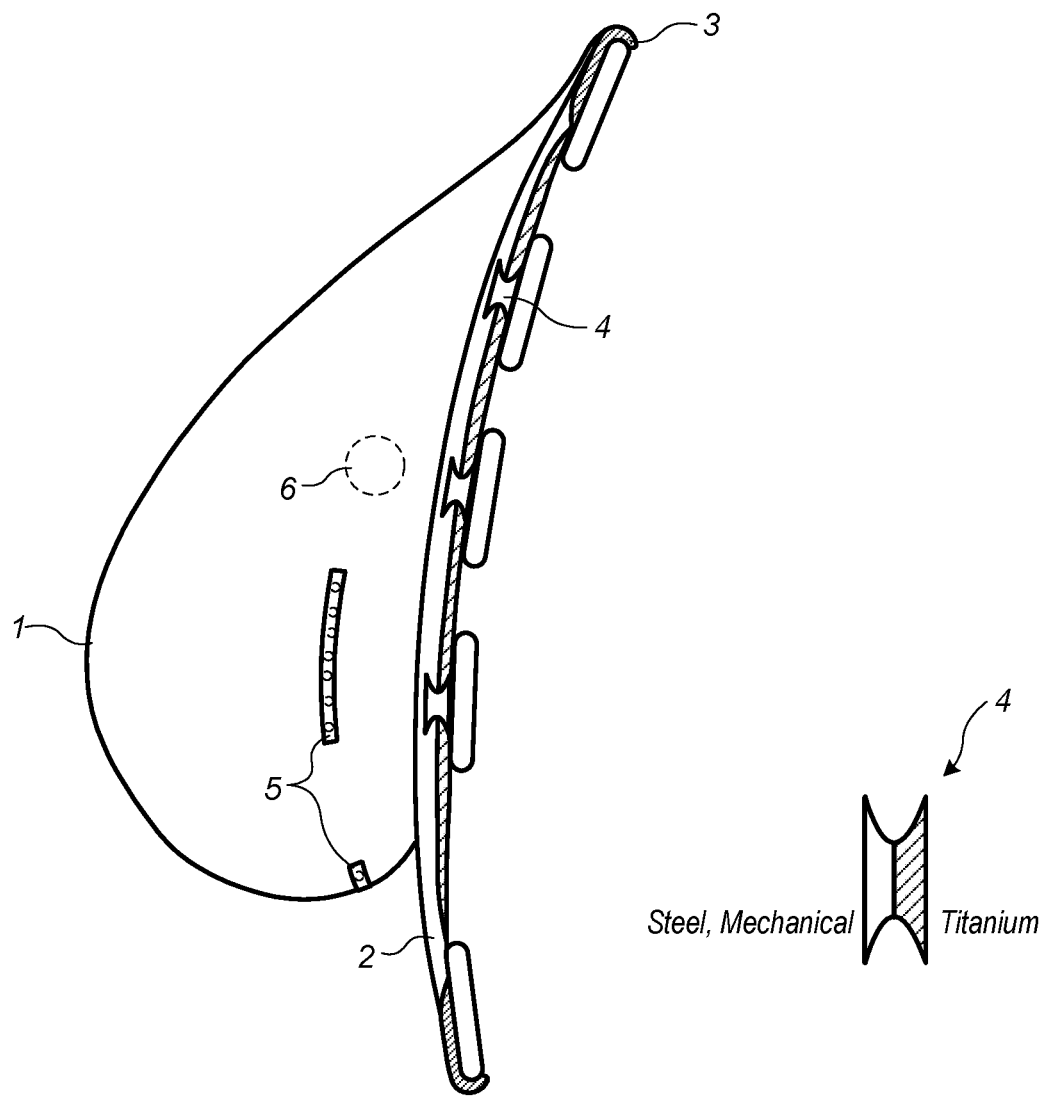
FIG. 3 depicts a side view of a breast implant attached to multiple ribs.

FIGS. 1-3 depict an embodiment of a breast implant for altering the appearance of a patient's breast. Breast implant includes a container 1 composed of an elastomeric material. Suitable elastomeric materials include, but are not limited to, silicone elastomers such as polydimethylsiloxane and polydiphenylsiloxane.

Container 1 defines an inner cavity (not shown). Inner cavity is filled with a liquid or gel filling material. Filling materials include, but are not limited to saline solutions and silicone gels.

A support member 2 is coupled to container 1. Support member 2 is formed as an integral part of container 2. As shown in the figures, support member 2 is integrated into the elastomeric material which formers the outer shell of container 1. In this manner, container 1 is completely supported by support member 2. Support member two may be composed of any biocompatible material. Preferably support member 2 is formed from a polymeric biocompatible material that has some elasticity. In one embodiment, the elasticity of support member 2 is such that the ribs can undergo expansion and contraction without any noticeable resistance from the attached support member. Suitable materials that may be used to form the support member include, but are not limited to, polyvinyl chloride, polytetrafluoroethylene polyethersulfone, polyethylene, polyurethane, polyetherimide, polycarbonate, polyether ether ketone, polysulfone, and polypropylene. The molecular weight, cross-linking and other properties of the selected polymeric biocompatible material may be chosen to create a support member having suitable elasticity, as discussed above, but also provides sufficient support for the breast implant to control movement of the implant.

Support member 2 may contact, or be embedded, in an elastomeric outer shell of the container along the longitudinal axis of the container 1. Support member 2 may therefore run perpendicular to the ribs, when implanted into the patient. Support member 2 may have a length which allows the support member to be coupled to 2 to 5 ribs.

As best shown in FIG. 3, support member 2 may be coupled to two or more ribs of the patient. Support member 2 may include one or more hooks 3 that surround a portion of the ribs securing the support member to the ribs. In the embodiment depicted in the figures, support member 2 includes two hooks 3 connected to the ends of the support member. In use, the hooks are used to couple support member 2 to a rib above the container and to a rib below the container, thus providing support throughout the length of the container. Hooks 3 may be formed from a biocompatible metal or plastic. Preferably, hooks 3 may be formed from titanium.

One or more fasteners 4 may also be used to connect the support member to the ribs. Fasteners 4 may couple support member 2 to the anterior side of the ribs. In one embodiment, fasteners 4 may be formed from a titanium/steel material, with the titanium material in contact with the rib and the steel material embedded in the elastomeric outer shell of the implant. The titanium portion of the fasteners may be glued or screwed into the ribs of the patient. Fasteners may also be used to alter the shape of the implant. Fasteners, in one embodiment, are couplable to any portion of support member 2. This may allow the container to be mounted higher or lower along the support member. Being able to alter the position of the support member may allow better position during the surgical procedure, as well as allowing the surgeon to alter the physical shape of the container to create the desired appearance of the altered breast.

In some embodiments, the breast implant may include one or more stichable regions 5, which can receive threading (e.g., sutures). Stichable regions 5 may include a number of slits and or loops which can be used to secure the threading to the implant. The treading may be used to alter the shape of the container and/or provide additional support for the container. The threading may be used to replicate Cooper's ligaments that are naturally present in breasts. Ports 6 may also be placed in container 1. Ports 6 may be used to empty or fill container 1 with the appropriate liquid or gel filling material.

The use of titanium for hooks 4 and fasteners 5 allows the bone to grow over and secure support member 2 to the bone naturally. Hooks 4 can be connected to the ribs without the need for drilling of the ribs themselves. Hooks 4 are eventually secured to ribs by new bone growth over the hooks. As more bone grows over the hooks and fasteners, the bonding strength of the implant to the ribs is increased. Bone deposits are generally rapid and the support member may be completed bonded by bone deposits in as little as 6 weeks. Generally, the support member will be fully integrated into the rib bone within about 6 months.

Breast implants, as depicted in FIGS. 1-3 may be implanted into the patient's body by coupling support member 2 onto two or more of the patient's ribs. Support member 2, and container 1 coupled to the support member, may be placed over the pectoralis major muscle and under the subglandular breast tissue. Alternatively, support member 2 and container 1 may be placed under the pectoralis major muscle. In an embodiment, support member 2 is placed under the muscle while container 2 is between the muscle and the subglandular breast tissue. In this embodiment, support member 2 may not be noticeable, since the support member is hidden by the muscle tissue. As discussed above, support member 2 may be coupled to the ribs of the patient using two or more hooks 4 and one or more fasteners 5.

It should be understood that, while depicted as a generally rectangular shape, support member 2 may be any suitable shape that can be coupled to the patient's ribs. For example, support member may have a "Y" shape or "X" shape, with a portion of the "Y" or "X" integrated with the container. Other configurations of straps may be used to create a more natural connection of the implant to the patient.

As shown in the figures, the described embodiments allow breast implants to mimic natural breast tissue more realistically by having a more natural shape and movement.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A breast implant for altering the appearance of a patient's breast comprising:
   a container composed of an elastomeric material, the container defining an inner cavity, wherein the inner cavity is filled with a liquid or gel filling material; and
   a support member coupled to the container, wherein the support member is an integral part of the container, and wherein the support member is couplable to two or more ribs of the patient, and wherein the support member comprises one or more fasteners that can be connected to the ribs of the patient.

2. The breast implant of claim 1, wherein the support member contacts the container over a majority of a longitudinal axis of the container.

3. The breast implant of claim 1, wherein the inner cavity comprises a saline solution.

4. The breast implant of claim 1, wherein the inner cavity comprises a silicone gel.

5. The breast implant of claim 1, wherein the support member is composed of a biocompatible polymer.

6. The breast implant of claim 1, wherein the container comprises a stichable region, wherein the stichable region receives threading that is used to alter the shape of the container and/or provide additional support for the container.

7. The breast implant of claim 1, wherein the container comprises a port, wherein liquid or gel filling material may be inserted or removed from the container through the port.

8. A method of implanting a breast implant comprising: coupling a breast implant to two or more of the ribs of the patient, wherein the breast implant comprises:
 a container composed of an elastomeric material, the container defining an inner cavity, wherein the inner cavity is filled with a liquid or gel filling material; and
 a support member coupled to the container, wherein the support member is an integral part of the container;
 wherein the breast implant is implanted over the pectoralis major muscle and under the subglandular breast tissue.

9. The method of claim 5, wherein coupling the support member to two or more ribs comprises attaching two or more hooks of the support member to the ribs of the patient.

10. The method of claim 5, wherein the support member comprises one or more biocompatible hooks that couple the support to the ribs of the patient.

11. The method of claim 5, wherein the support member comprises one or more fasteners that can be connected to the ribs of the patient.

12. The method of claim 5, wherein the container comprises a stichable region, wherein the stichable region receives threading that is used to alter the shape of the container and/or provide additional support for the container.

13. The method of claim 5, wherein the container comprises a port, wherein liquid or gel filling material may be inserted or removed from the container through the port.

14. A breast implant for altering the appearance of a patient's breast comprising:
 a container composed of an elastomeric material, the container defining an inner cavity, wherein the inner cavity is filled with a liquid or gel filling material; and
 a support member coupled to the container, wherein the support member is an integral part of the container, and wherein the support member is couplable to two or more ribs of the patient, and wherein the support member comprises one or more biocompatible hooks that couple the support to the ribs of the patient.

15. The breast implant of claim 14, wherein the support member contacts the container over a majority of a longitudinal axis of the container.

16. The breast implant of claim 14, wherein the inner cavity comprises a saline solution.

17. The breast implant of claim 14, wherein the inner cavity comprises a silicone gel.

18. The breast implant of claim 14, wherein the support member is composed of a biocompatible polymer.

19. The breast implant of claim 14, wherein the container comprises a stichable region, wherein the stichable region receives threading that is used to alter the shape of the container and/or provide additional support for the container.

20. The breast implant of claim 14, wherein the container comprises a port, wherein liquid or gel filling material may be inserted or removed from the container through the port.

* * * * *